United States Patent
Ouchi

(10) Patent No.: US 6,338,717 B1
(45) Date of Patent: Jan. 15, 2002

(54) TIP OF ULTRASONIC ENDOSCOPE

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/466,918

(22) Filed: Dec. 20, 1999

(30) Foreign Application Priority Data

Dec. 22, 1998 (JP) .............................. 10-363838
Dec. 22, 1998 (JP) .............................. 10-363839
Dec. 22, 1998 (JP) .............................. 10-363840

(51) Int. Cl.[7] .............................................. A61B 8/12
(52) U.S. Cl. ..................... 600/462; 600/464; 600/461
(58) Field of Search ................... 600/439, 447, 600/461–464, 104, 106, 107, 153, 170

(56) References Cited

U.S. PATENT DOCUMENTS 5,471,988 A * 12/1995 Fujio et al. ................. 600/463

FOREIGN PATENT DOCUMENTS

| JP | 2-265533 | 10/1990 | |
| JP | 2-265534 | 10/1990 | |
| JP | 2-265535 | 10/1990 | |
| JP | 8-131442 | 5/1996 | |
| JP | 8-140976 | * 6/1996 | ............ A61B/8/12 |

* cited by examiner

Primary Examiner—John Mulcahy
(74) Attorney, Agent, or Firm—Greenblum & Bernstein P.L.C.

(57) ABSTRACT

A radially scanning, annular ultrasonic oscillator array is provided in a tip body of an endoscope so as to be arranged about the longitudinal axis of the tip body. A first treatment tool projection port is provided in the tip body and opens at a location longitudinally forward from a location where the annular ultrasonic oscillator array is provided. A second treatment tool projection port is provided to the tip body and opens at a location longitudinally rearward from the location where the annular ultrasonic oscillator array is provided.

12 Claims, 9 Drawing Sheets

TIP OF ULTRASONIC ENDOSCOPE

BACKGROUND OF THE INVENTION

The present invention relates to the tip of an ultrasonic endoscope hating a radially scanning annular ultrasonic oscillator array provided at the distal end of the insertion portion.

Ultrasonic endoscopes are capable of optical examination of the surface of a membrane in a body cavity while producing an ultrasonic cross-sectional image of the tissue under the membrane They are tools useful not only for inspection but also for surgical treatment.

The ultrasonic endoscopes that serve these purposes are provided with not only a system for optical examination and a system for ultrasonic scanning but also a system for projecting treatment tools such as an injecting syringe.

Surgical treatment with endoscopes is called an endoscopic treatment and its kind and the scope of its application vary considerably depending upon whether two treatment tools can be projected from the endoscope simultaneously. For endoscopic treatment, ultrasonic endoscopes are desirably equipped with two channel and port sets for projecting treatment tools simultaneously.

However, a known ultrasonic endoscope is provided with an ultrasonic scanning system that is different from ordinary endoscopes. It has heretofore been difficult to provide the ultrasonic endoscope with a plurality of treatment tool projecting systems because such will further increase the size of the distal end of the insertion portion and thus causes great pain to the patient.

A first object, therefore, of the present invention is to provide the tip of an ultrasonic endoscope that is not unduly bulky at the distal end of the insertion portion and which is yet capable of high-level endoscopic treatment with two treatment tools being projected simultaneously.

With respect to reducing the size of the distal end of the insertion portion of an ultrasonic endoscope, it has been proposed by Japanese Patent Unexamined Publication No. Hei. 2-265533 to use an annular ultrasonic oscillator array for radial scanning, and to arrange optical members and a treatment tool projection port at a joint between adjacent ultrasonic oscillators.

Ultrasonic wave signals are not effectively transmitted through air. In order to perform ultrasonic scan within a body cavity, it is recommended that a balloon filled with deaerated or degasified water or the like be placed around the ultrasonic oscillator array and ultrasonic wave signals be transmitted and received through the balloon being pressed against the membrane in the body cavity.

However, if treatment tool projection port is provided between adjacent ultrasonic oscillators as in the arrangement disclosed by Japanese Patent Unexamined Publication No. Hei. 2-265533, the treatment tool, such as an injecting syringe, projecting from the port punctures the balloon and effective balloon-assisted ultrasonic examination cannot be performed A second object, therefore, of the present invention is to provide the tip of an ultrasonic endoscope that uses a radial scanning, annular ultrasonic oscillator array, and which is capable of effective ultrasonic examination with a balloon attached so that the balloon is not potentially damaged with treatment tools.

The ultrasonic endoscope provided with a radial scanning, annular ultrasonic oscillator array suffers from another problem: Since the direction of ultrasonic scan lies in a plane normal to the longitudinal axis of the distal end of the insertion portion, the tip of a treatment tool must be guided and projected from the distal end of the insertion portion at an angle almost equal to 90 degrees.

This requirement causes the treatment tool to have the habit or tendency to bend and hinders smooth guiding of the tip of the endoscope to an aimed part. Further, since great resistance develops as the treatment tool is inserted into or removed out of the channel, the treatment tool may often buckle or otherwise break at the end which is closer to the operator.

A third object, therefore, of the present invention is to provide the tip of an ultrasonic endoscope that is equipped with a radial scanning, annular ultrasonic oscillator array and which permits treatment tools to project smoothly with limited occurrence of fatigue and breakage.

SUMMARY OF THE INVENTION

The present invention provides an arrangement for a tip of an ultrasonic endoscope, in which a treatment tool projection port is provided at a location longitudinally forward from a location where a radial scanning, annular ultrasonic oscillator array is provided. This arrangement makes it possible to prevent a treatment tool from damaging a balloon mounted around the annular ultrasonic oscillator array.

The present invention further provides an arrangement for a tip of an ultrasonic endoscope, in which two treatment tool projection ports are provided, one being located longitudinally forward from a location where a radial scanning, annular ultrasonic oscillator array is provided, and the other being located longitudinally rearward from the location where the annular ultrasonic oscillator is provided. This arrangement permits two treatment tools to project simultaneously from the tip of the endoscope without substantively increasing the size of the tip of the endoscope, thereby providing efficient endoscopic treatment.

The present invention further provides an arrangement for a tip of an ultrasonic endoscope, in which a radial scanning, annular ultrasonic oscillator array is arranged inclined, and a treatment tool projection port is provided at a location longitudinally rearward from a location where the annular ultrasonic oscillator array is provided. This arrangement make it possible to reduce an angle between a treatment tool projected from the treatment tool projection port and a longitudinal axis of the tip. Therefore, the treatment tool can project from the treatment tool projection port without great resistance, which would otherwise cause fatigue or damage of the treatment tool.

The present disclosure relates to the subject matter contained in Japanese patent application Nos. Hei. 10-363838, 10-363839 and 10-363840 (all filed on Dec. 22, 1998), all of which are expressly incorporated herein by reference in their entireties.

DESCRIPTION OF THE PREFERRED EMBODIMENT

Embodiments of the invention are described below with reference to the accompanying drawings.

Figure 1:
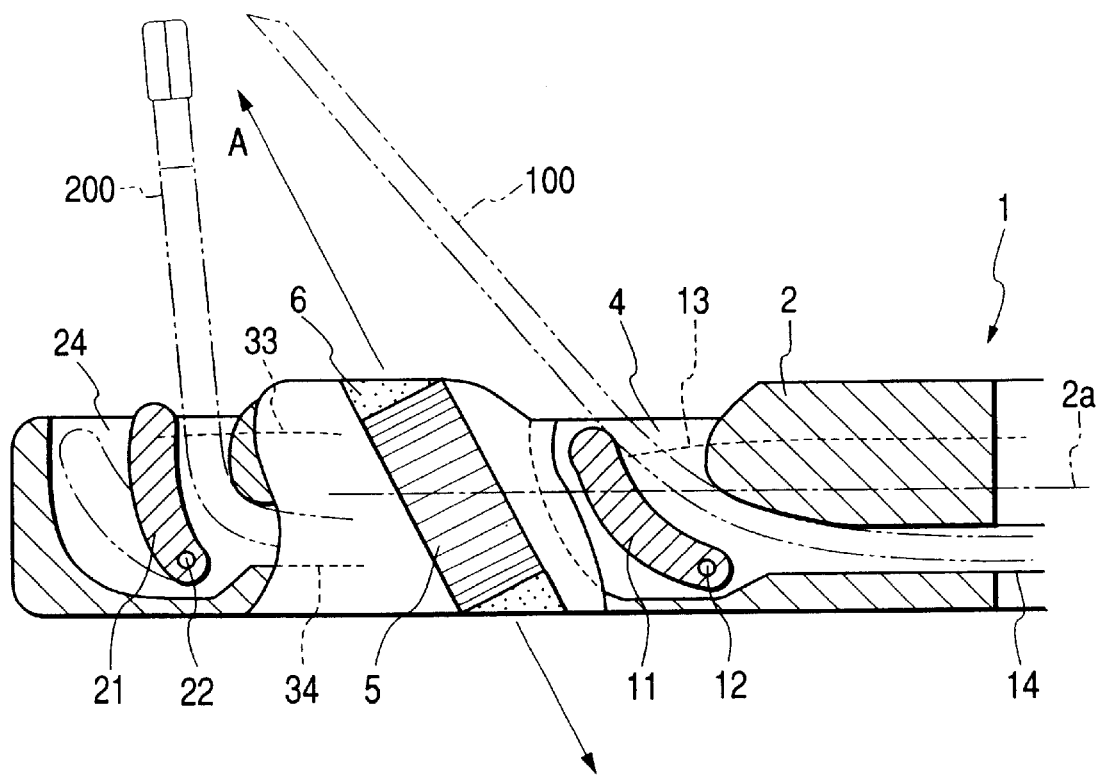
FIG. 1 is a section I—I of FIG. 3 which shows a tip of an ultrasonic endoscope according to a first embodiment of the invention.
Figure 2:
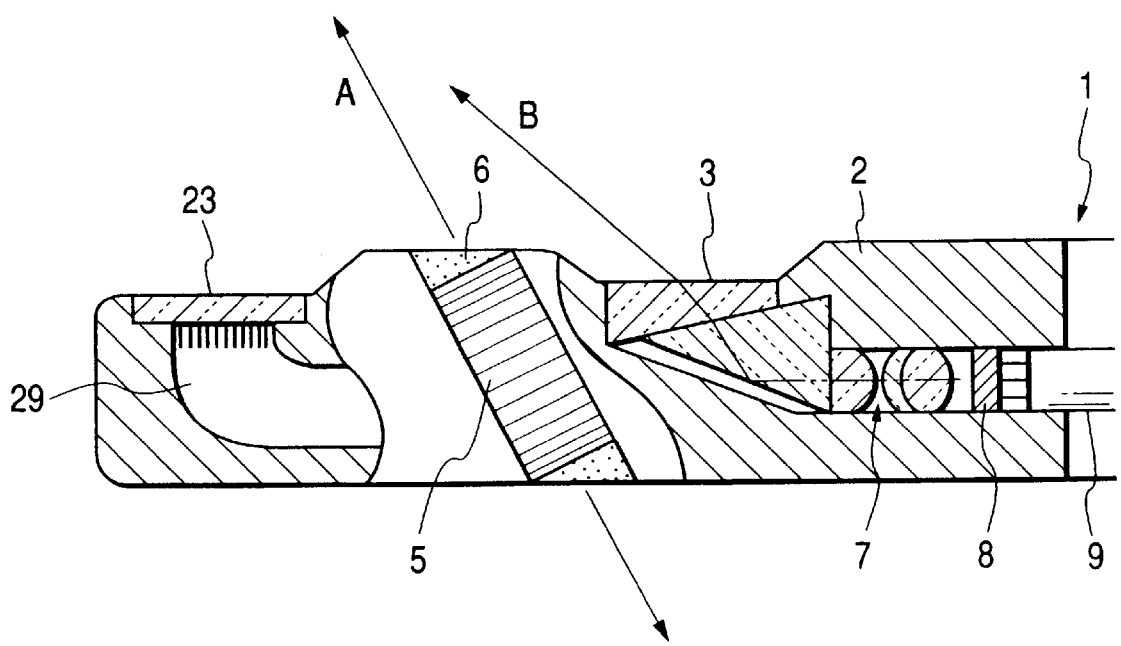
FIG. 2 is a section II—II of FIG. 3.
Figure 3:
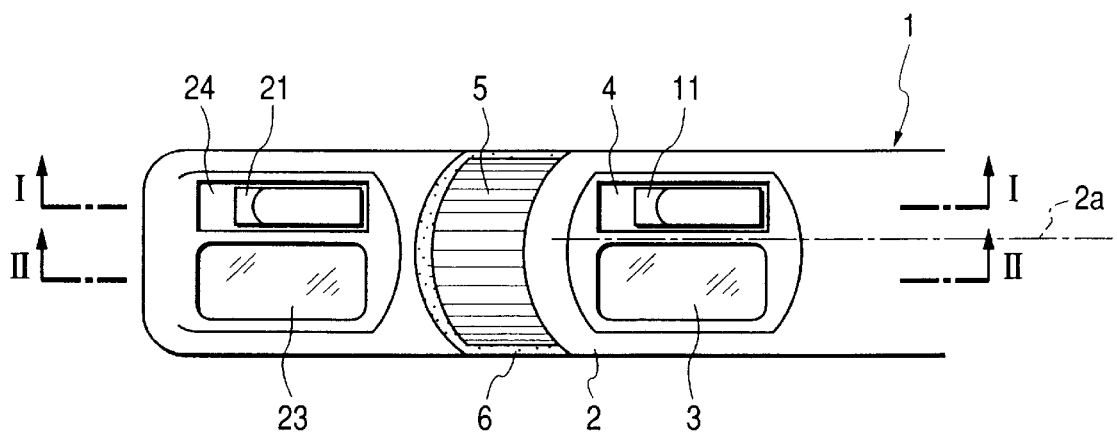
FIG. 3 is a plan view of the tip of the ultrasonic endoscope.

FIG. 3 is a plan view of the tip of an ultrasonic endoscope according to a first embodiment of the invention. FIG. 1 is section I—I of FIG. 3 and FIG. 2 is section II—II of FIG. 3.

An insertion portion 1 of the ultrasonic endoscope has a tip body 2 attached as the distal end of the insertion portion 1. An annular ultrasonic oscillator array 5 for performing a radial scan is provided in the middle of the tip body 2. The ultrasonic oscillator array 5 is provided obliquely with respect to a longitudinal axis 2a of the tip body 2. As a result, the direction of ultra scan which is indicated by arrow A is not normal to but inclined with respect to the longitudinal axis 2a of the tip body 2.

The ultrasonic oscillator array 5 is made up of cylindrically arranged ultrasonic oscillators that are segmented radially to transmit and receive ultrasonic wave signals alternatively (i.e., radial ultrasonic scan).

The surface of the ultrasonic oscillator array 5 is recessed compared to the surface of tip body 2 and, hence, filled with polymethylpentene 6 or some other material that is highly transparent to ultrasonic waves.

As is clear from FIG. 3, an optical viewing window 3 and a first treatment tool projection port 4 are provided on the side of the tip body 2 in an area backward of the ultrasonic oscillator array 5 and they are on opposite sides of the longitudinal axis 2a of the tip body 2. An illumination window 23 and a second treatment tool projection port 24 are also provided on the side of the tip body 2 but in an area ahead of the ultrasonic oscillator array 5; i.e., they are on opposite sides of the longitudinal axis 2a of the tip body 2.

Thus, the first treatment tool projection port 4 and the second treatment tool projection port 24 are respectively provided backward of and ahead of the ultrasonic oscillator array 5 whose ultrasonic scan direction A is oriented obliquely forward. As is clear from FIG. 2, the viewing axis B of the viewing optics, which extends from the viewing window 3, is oriented obliquely forward similar to the ultrasonic scan direction A, so that an object subjected to the ultrasonic scan can be visually observed through the viewing optics. That is, the viewing optics are designed to view an object located obliquely forward from the viewing window 3.

Provided interior to the optical viewing window 3 are objective optics 7 comprising a prism and lens combination (see FIG. 2) and the imaging plane of a solid-state imaging device 8 is provided in the position where the image of an object is formed by means of the objective optics 7. Indicated by 9 is a signal cable. If desired, the solid-state imaging device 8 maybe replaced by an imageguide fiber bundle.

Provided interior to the illumination window 23 is the exit end of a lightguide fiber bundle 29 for illuminating the object. If desired, the positions of the viewing window 3 and the illumination window 23 may be reversed.

The direction in which a distal end of a treatment tool 100, 200 projects is adjusted by means of a treatment tool erecting plate 11, 21. As is clear from FIG. 1, a treatment tool erecting plate 11, 21 is provided within the treatment tool projection port 4, 24 in such a way that it is pivotal about a shaft 12, 22. The innermost end of the port 4, 24 is connected to the distal end of a first treatment tool insertion channel 14, 34 that is passed through the entire length of the insertion portion 1.

A treatment tool erecting plate 11, 21 is allowed to pivot by action of a manipulation wire 13, 33 that is moved back and forth by remote control from a manipulating section (not shown) that is coupled to the proximal end of the insertion portion 1 which is closer to the operator. As the treatment tool erecting plate 11, 21 pivots, the distal end of the treatment tool 100, 200 passed through the treatment tool insertion channel 14, 34 projects in a varying direction.

The second treatment tool insertion channel 24, manipulation wire 33, lightguide fiber bundle 29 and the like are provided to pass through the space interior to the ultrasonic oscillator array 5 and, hence, the tip body 2 is formed in a compact and small size.

Figure 4:
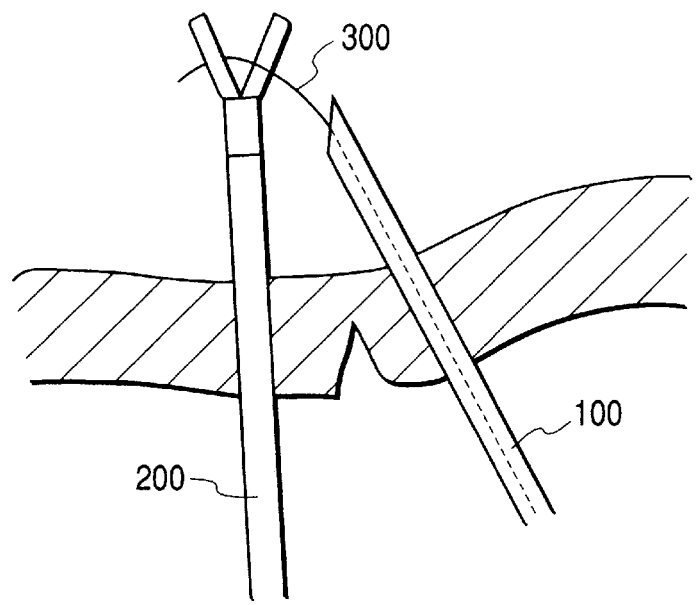
FIG. 4 shows how the first part of an endoscopic treatment is performed using the ultrasonic endoscope.
Figure 5:
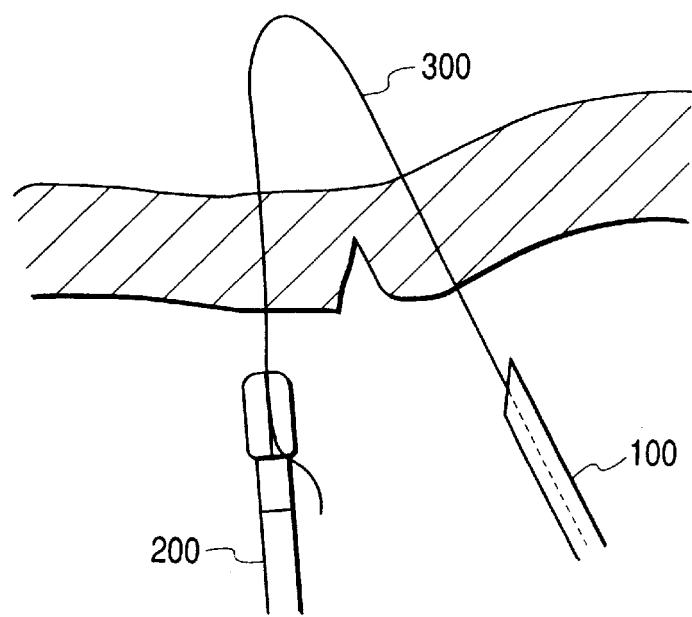
FIG. 5 shows how the second part of the endoscopic treatment is performed.

FIG. 4 shows one way to use the surgical ultrasonic endoscope according to the first embodiment of the invention. A tubular puncturing needle 100 and grasping forceps 200 are allowed to project from the respective treatment tool projection ports 4 and 24 so that they are pierce a membrane. A suture 300 delivered through the bore of the needle 100 is grasped with the forceps 200 on the other side of the membrane and, thereafter, the needle 100 and the forceps 200 are pulled back (see FIG. 5) to stitch the wound in the membrane. Other kinds of high-level endoscopic treatment can be performed using the surgical ultrasonic endoscope according to the first embodiment of the invention.

Figure 6:
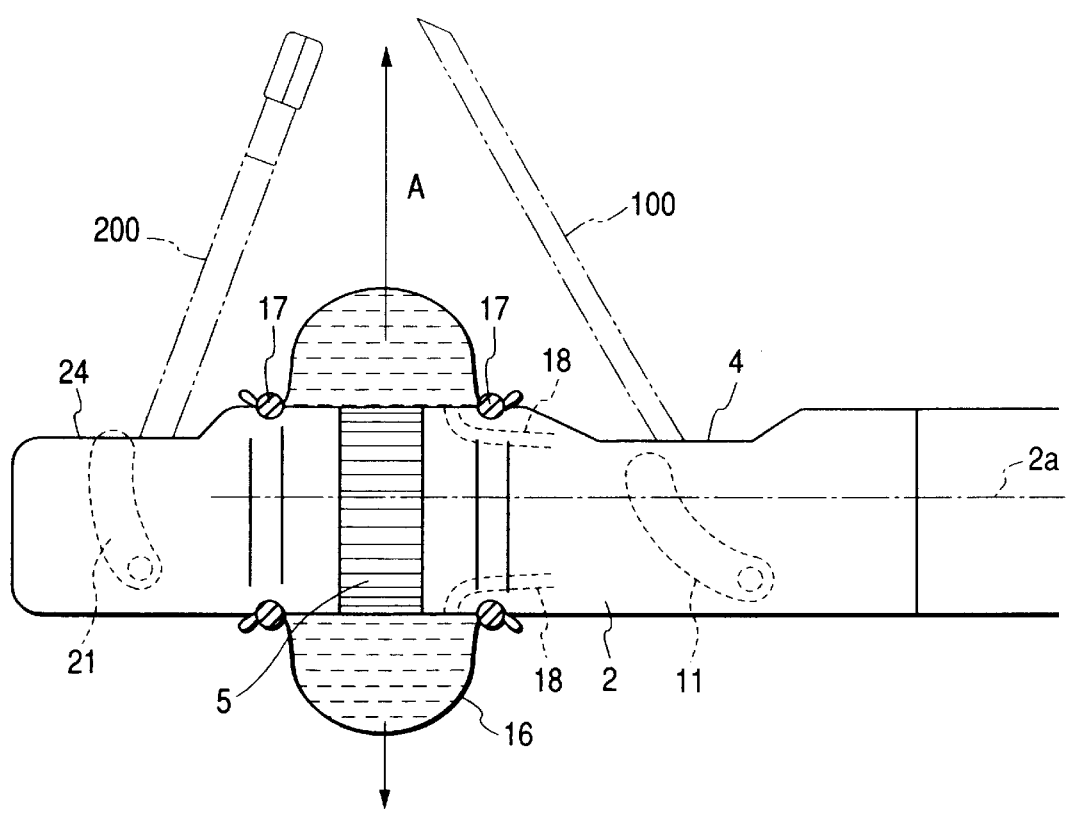
FIG. 6 is a side view of a tip of an ultrasonic endoscope according to a second embodiment of the invention.

FIG. 6 shows the tip of a surgical ultrasonic endoscope according to a second embodiment of the invention, in which the annular ultrasonic oscillator array 5 is provided coaxially with the longitudinal axis of the tip body 2. In the second embodiment, the ultrasonic scan direction A is in a plane normal to the longitudinal axis of the tip body 2 and the surface of the ultrasonic oscillator array 5 is flush with the tip body 2, providing no recess.

In the second embodiment of the invention, an inflatable balloon 16 is made of an elastic thin rubber material and detachably provided on the tip body 2 by O-rings or rubber bands 17 in such a way as to surround the ultrasonic oscillator array 5.

The balloon 16 is inflated by filling it with a liquid such as deaerated water through water supplying and discharging tubes 18 and pressed against the membrane in a body cavity to eliminate an intervening air layer; which contributes to produce a sharp, ultrasonic cross-sectional image. The second embodiment of the invention is otherwise similar to the first embodiment. If desired, the balloon 16 may be attached to the tip body 2 constructed in accordance with the first embodiment.

Figure 7:
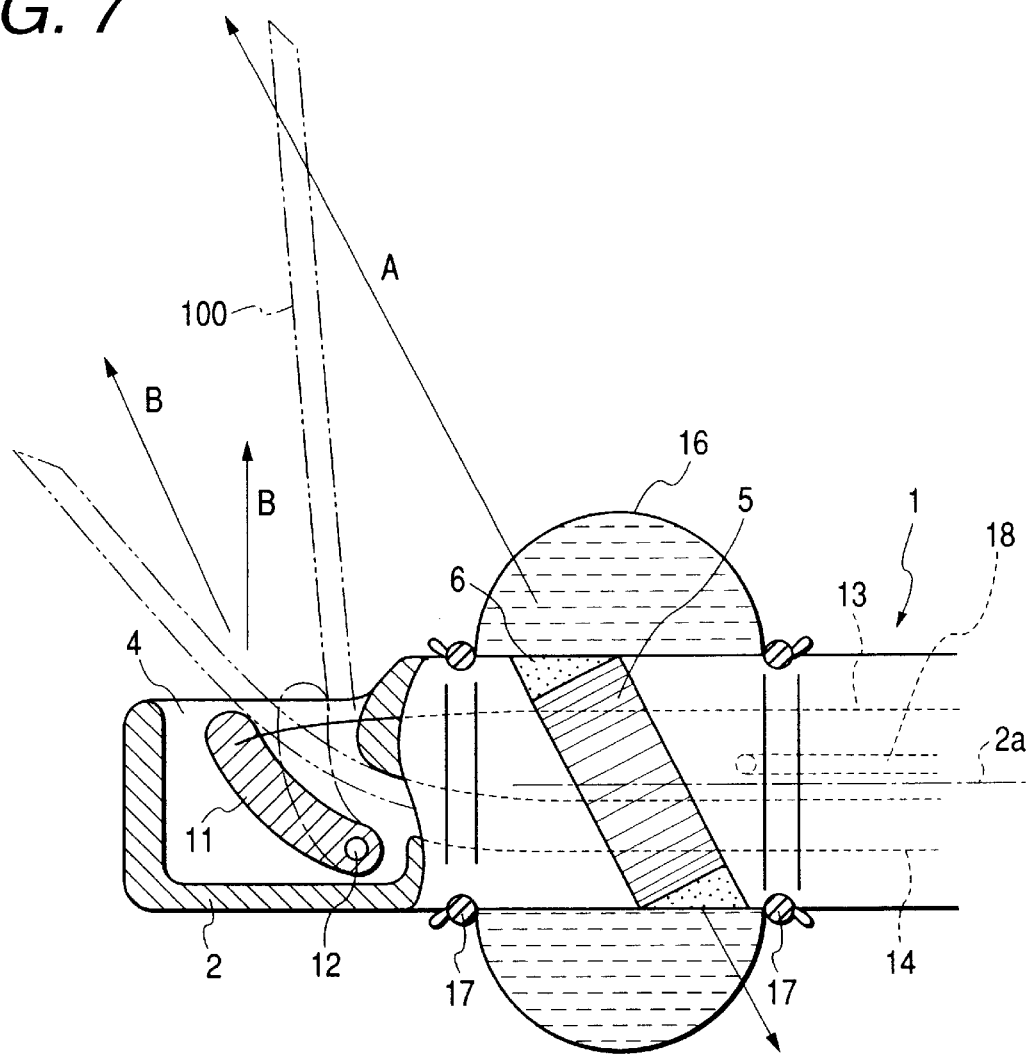
FIG. 7 is a sectional side view of a tip of an ultrasonic endoscope according to a third embodiment of the invention.
Figure 8:
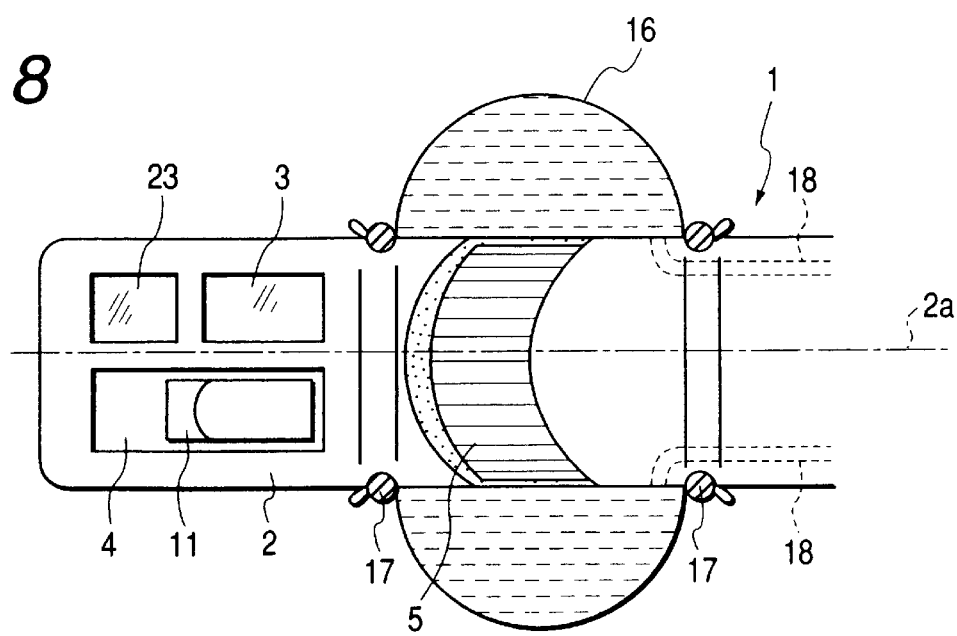
FIG. 8 is a plan view of the tip of the ultrasonic endoscope shown in FIG. 7.

FIGS. 7 and 8 show the tip of an ultrasonic endoscope constructed according to a third embodiment. In the third embodiment, the optical viewing window 3, the treatment tool projection port 4 and the illumination window 23 are provided ahead of the ultrasonic oscillator array 5, the array having an inclined ultrasonic scan direction A. As shown in FIG. 8, the optical viewing window 3 is located opposite the treatment tool projection port 4 with respect to the longitudinal axis 2a of the tip body 2. The viewing axis B of the viewing optics, which extends from the viewing window 3 may be inclined forwardly or directed orthogonal to the longitudinal axis 2a of the tip body 2 so that an object subjected to the ultrasonic scan can be simultaneously observed through the viewing optics. The treatment tool insertion channel 14, manipulation wire 13, lightguide fiber bundle or image signal transmission cable (9, not shown in FIGS. 7 and 8), illumination lightguide fiber bundle (29, not shown in FIGS. 7 and 8) and the like are provided to pass through the space interior to the ultrasonic oscillator array 5. Water supplying and discharging tubes 18 pass through the insertion portion 1 to supply or discharge deaerated water to or from the interior of the balloon 16.

Since the treatment tool 100 projects obliquely forward from a location ahead of the balloon 16, the treatment tool 100 does not puncture the balloon 16.

To direct the distal end of the treatment tool 100 toward an object observed through the optical viewing window 3, the treatment tool erecting plate 11 is manipulated. Since the ultrasonic scan direction A is oriented obliquely forward, it is not necessary to erect the distal end of the treatment tool 100 extremely rearward by the erecting plate 11. Thus, resistance can be reduced when the treatment tool 100 is inserted into or removed out of the treatment tool insertion channel.

Figure 9:
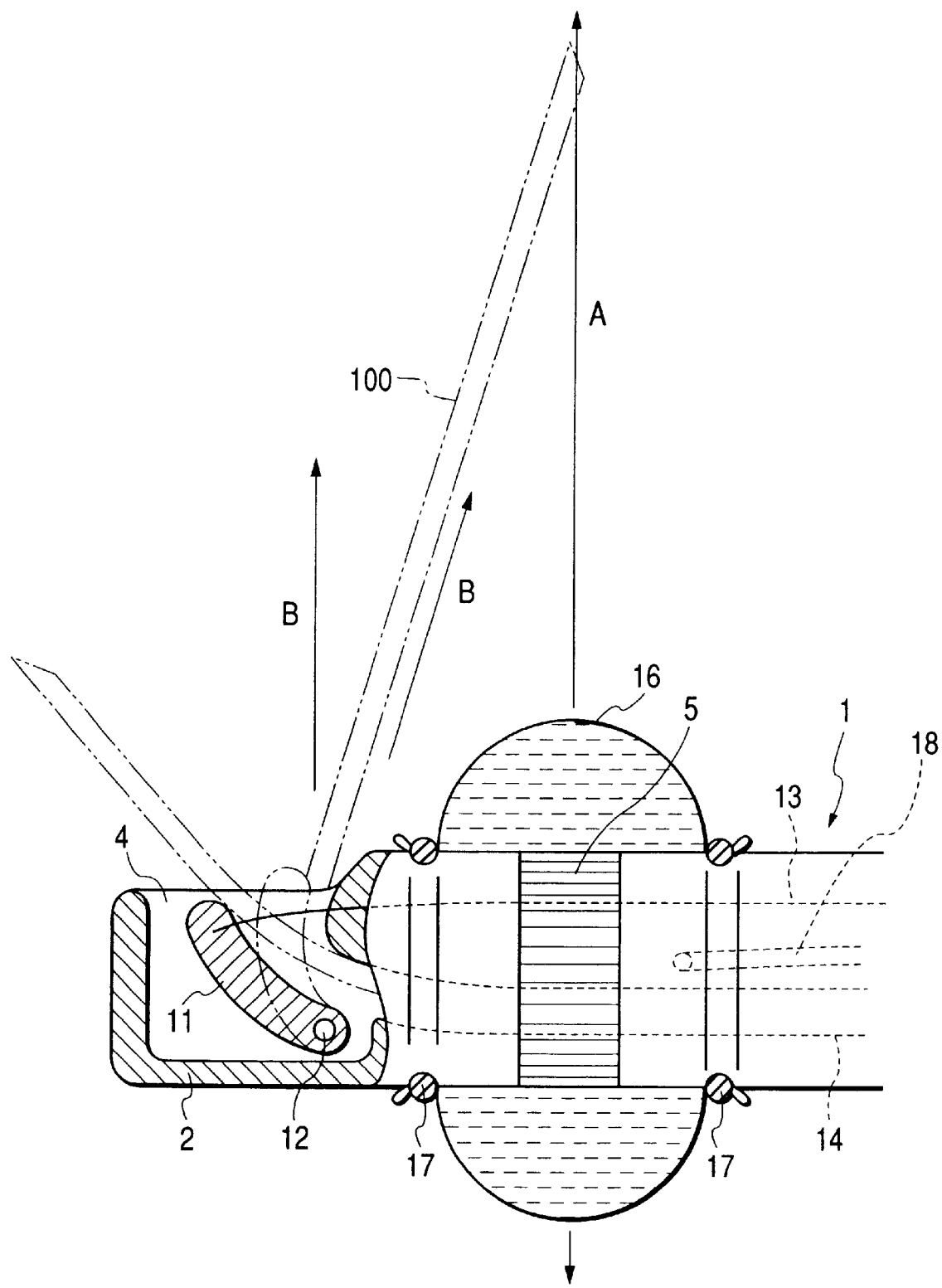
FIG. 9 is a sectional side view of a tip of an ultrasonic endoscope according to a fourth embodiment of the invention.
Figure 10:
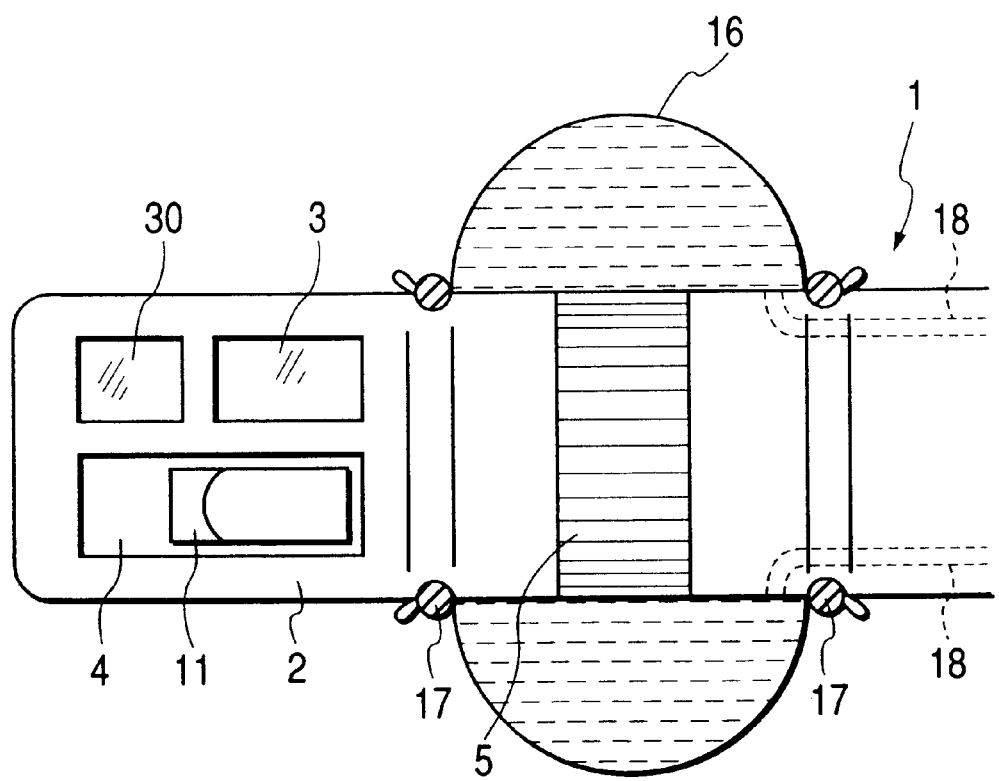
FIG. 10 is a plan view of the tip of the ultrasonic endoscope shown in FIG. 9.

FIGS. 9 and 10 show the tip of an ultrasonic endoscope constructed according to a fourth embodiment, in which the annular ultrasonic oscillator array 5 is provided coaxially with the longitudinal axis of the tip body 2 similarly to the second embodiment. In this case, it is preferable to design the viewing optics such that the viewing axis B extends substantially orthogonal to the longitudinal axis of the tip body 2 or obliquely rearward with respect to the longitudinal axis of the tip body 2. Other constructions of the fourth embodiment are the same as or similar to those of the third embodiment. The fourth embodiment is also constructed so that balloon 16 is prevented from being damaged by the treatment tool 100.

Figure 11:
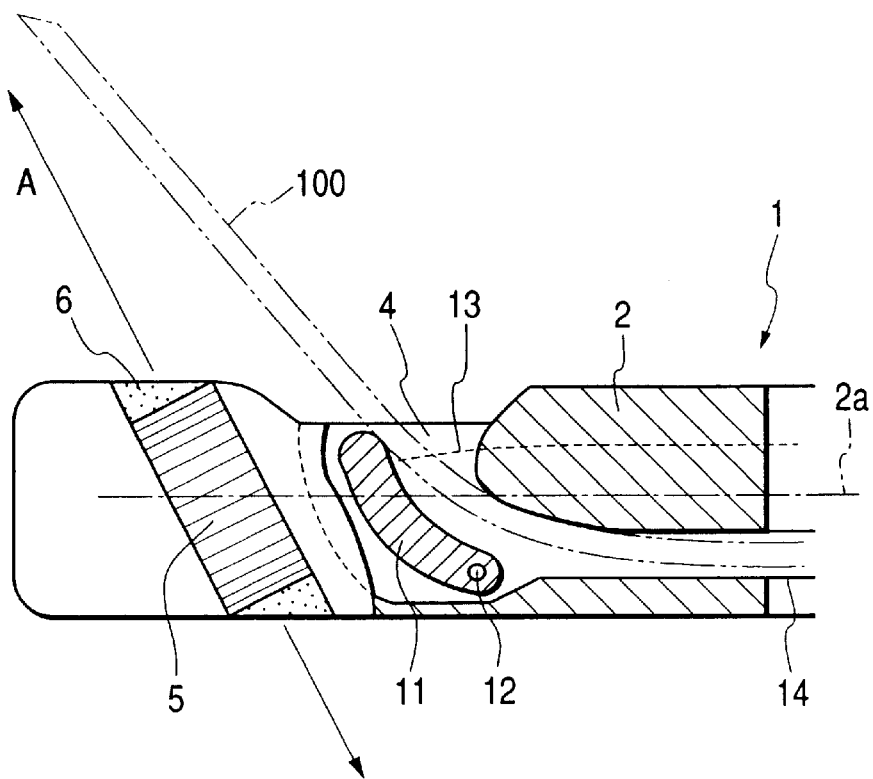
FIG. 11 is a section I—I of FIG. 13 which shows a tip of an ultrasonic endoscope according to a fifth embodiment of the invention.
Figure 12:
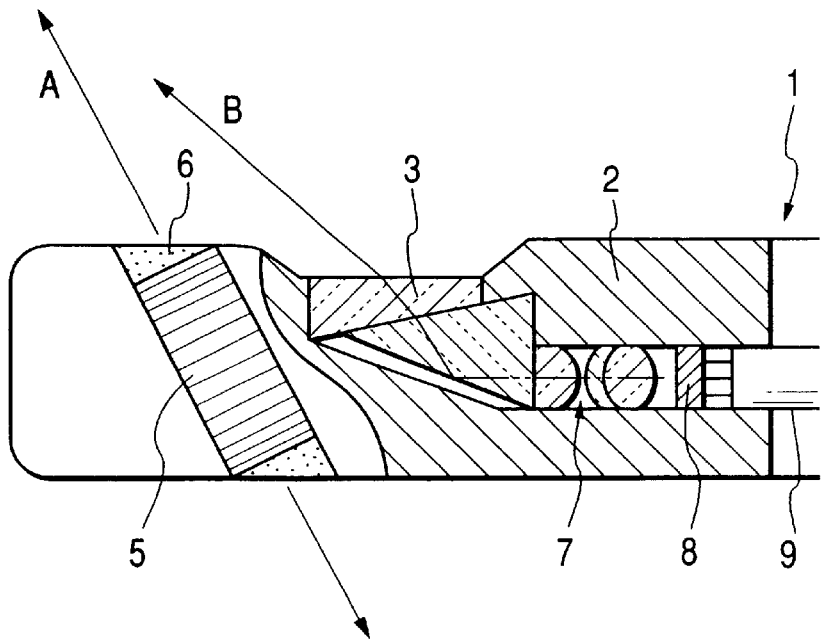
FIG. 12 is a section II—II of FIG. 13.
Figure 13:
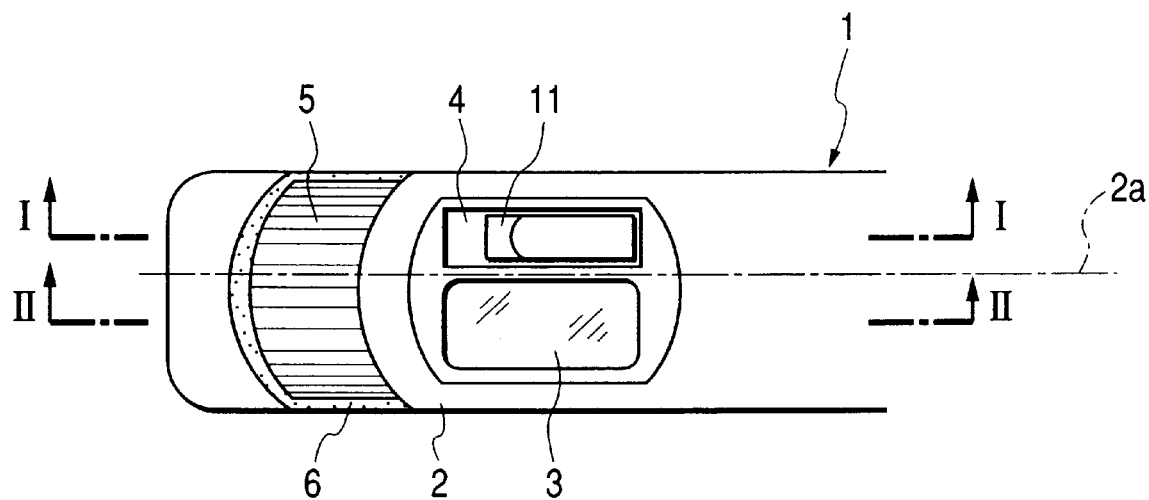
FIG. 13 a plan view of the tip of the ultrasonic endoscope.

FIGS. 11, 12 and 13 show the tip of an ultrasonic endoscope constructed according to a fifth embodiment. The viewing optical window 3 and the treatment tool projection port 4 are provided in an area backward of the ultrasonic oscillator array 5, the array having an inclined ultrasonic scan direction A. As shown in FIG. 13, the optical viewing window 3 is located opposite the treatment tool projection port 4 with respect to the longitudinal axis 2a of the tip body 2.

Since the treatment tool 100 projects obliquely forward from a location backward of the ultrasonic oscillator array 5 whose ultrasonic scan direction A is directed obliquely forward, the erecting angle of the treatment tool 100 with respect to the longitudinal direction of the tip body 2 can be reduced. Therefore, the treatment tool 100 can project from the endoscope without great resistance which would otherwise cause the treatment tool 100 to buckle or break.

Figure 14:
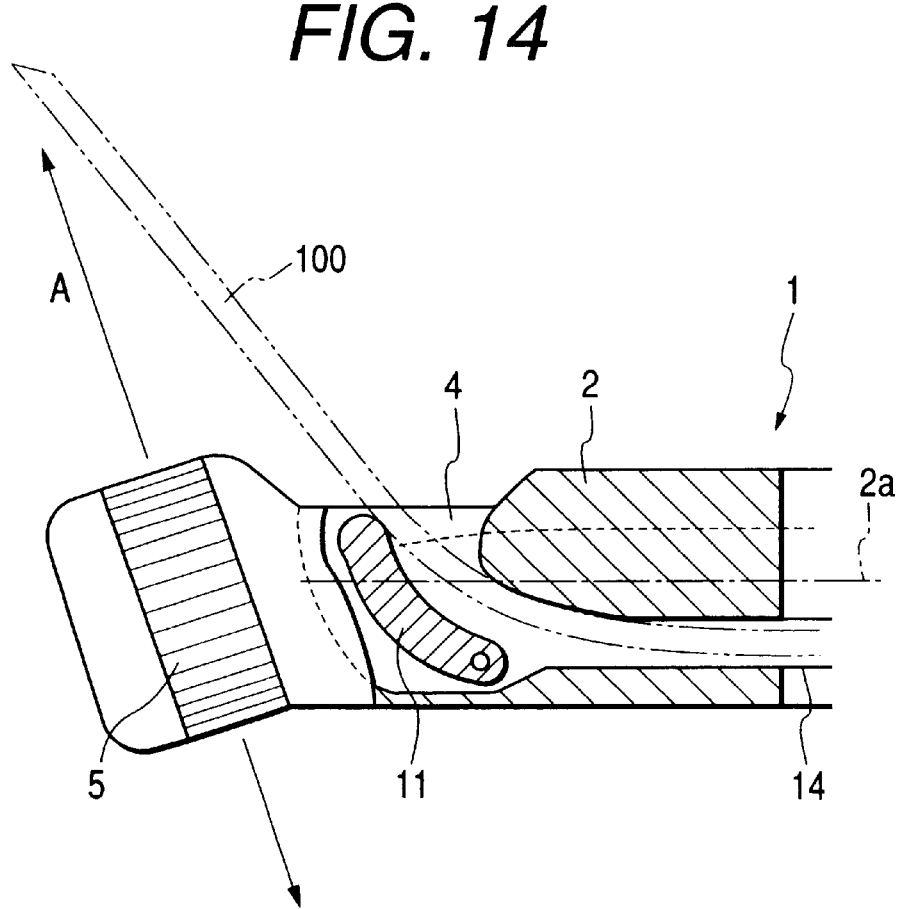
FIG. 14 is a sectional side view of a tip of an ultrasonic endoscope according to a sixth embodiment of the invention.

FIG. 14 shows the tip of an ultrasonic endoscope according to a sixth embodiment, in which a part of the tip body 2 where the ultrasonic oscillator array 5 is installed is arranged inclined with respect to the longitudinal direction 2a of the tip body 2, so that the inclination of tip body conforms with the inclination of the ultrasonic oscillator array 5. The surface of the ultrasonic oscillator array 5 is flush with the surface of the tip body, providing no recess. Other constructions of the sixth embodiment are the same as or similar to those of the fifth embodiment.

Figure 15:
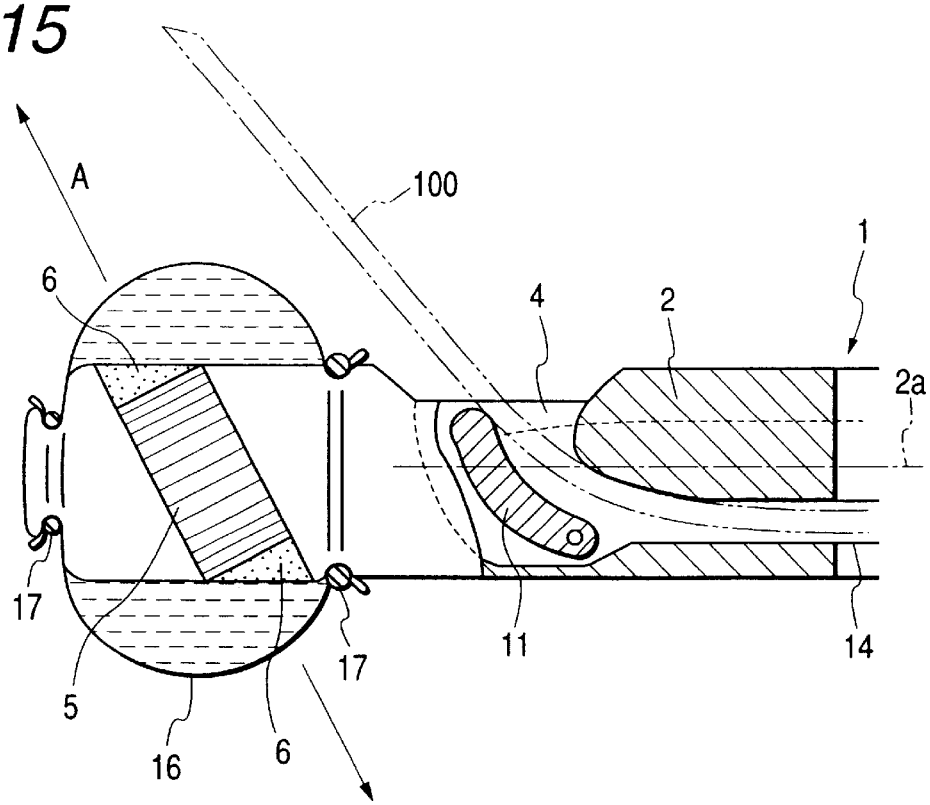
FIG. 15 is a sectional side view showing a state where the fifth embodiment is used in combination with a balloon.

FIG. 15 shows a state where the fifth embodiment is used in combination with the balloon 16.

Figure 16:
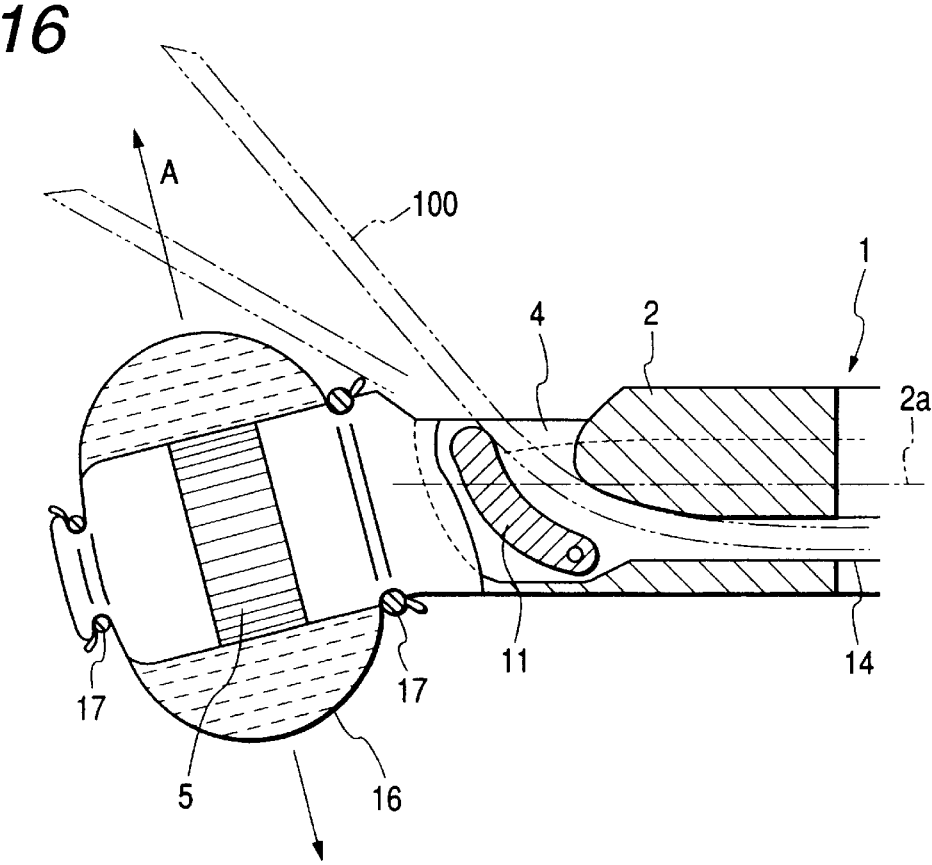
FIG. 16 is a sectional side view showing a state where the sixth embodiment is used in combination with a balloon.

FIG. 16 shows a state where the sixth embodiment is used in combination with the balloon 16. Since the part of the tip body 2 where the balloon 16 is installed is inclined to avoid the interference of the balloon 16 with the distal end of the treatment tool 100, this arrangement is effective to prevent the treatment tool 100 from puncturing the balloon 16.

What is claimed is:

1. A tip of an ultrasonic endoscope, comprising:
   a tip body having a longitudinal axis;
   a radial scanning, annular ultrasonic oscillator array provided in the tip body and arranged about the longitudinal axis;
   a first treatment tool projection port provided in the tip body and having an opening at a location longitudinally forward from the location of the annular ultrasonic oscillator array; and
   a second treatment tool projection port provided in the tip body and having an opening at a location longitudinally rearward from the location of the annular ultrasonic oscillator array.

2. The tip according to claim 1, further comprising:
   at least one treatment tool erecting plate disposed within at least one of the first and second treatment tool projection ports.

3. The tip according to claim 1, further comprising:
   a balloon provided on the tip body and surrounding the annular ultrasonic oscillator.

4. The tip according to claim 1, further comprising:
   an optical viewing window provided to the tip body and adjacent one of the first and second treatment tool projection ports.

5. The tip according to claim 1, wherein an axis of the annular ultrasonic oscillator array is inclined with respect to the longitudinal axis.

6. A tip of an ultrasonic endoscope, comprising:
   a tip body having a longitudinal axis;
   a radially scanning, annular ultrasonic oscillator array provided in the tip body; and
   a first treatment tool projection port provided in one side of the tip body and having an opening at a location longitudinally rearward from a location where the annular ultrasonic oscillator array is provided;
   wherein the annular ultrasonic oscillator array has a scanning axis directed obliquely forward with respect to the longitudinal axis on the side of the first treatment tool projection port.

7. The tip according to claim 6, wherein a distal end of a treatment tool projects obliquely forward from the first treatment tool projection port when the treatment tool is passed through a treatment tool insertion channel of the endoscope.

8. The tip according to claim 6, wherein a part of the tip body where the annular ultrasonic oscillator array is installed is inclined coaxially with the axis of the annular ultrasonic oscillator array.

9. The tip according to claim 6, further comprising:
a balloon provided on the tip body and surrounding the annular ultrasonic oscillator.

10. The tip according to claim 6, further comprising:
an optical viewing window provided in the tip body and adjacent the first treatment tool projection port.

11. The tip according to claim 6, further comprising:
a second treatment tool projection port provided in the tip body and opening at a location longitudinally forward from the location where the annular ultrasonic oscillator array is provided.

12. The tip of an ultrasonic endoscope as in claim 6, the scanning axis of the annular ultrasonic oscillator array projecting forwardly with respect to the longitudinal axis.

* * * * *